United States Patent [19]

Johnson

[11] Patent Number: 5,371,092
[45] Date of Patent: Dec. 6, 1994

[54] USE OF PAROXETINE FOR THE TREATMENT OF SENILE DEMENTIA, BULIMIA, MIGRAINE OR ANOREXIA

[75] Inventor: Anthony M. Johnson, Welwyn, England

[73] Assignee: Beecham Group, p.l.c., New Horizons Court, England

[21] Appl. No.: 64,088

[22] PCT Filed: Nov. 21, 1991

[86] PCT No.: PCT/GB91/02062

§ 371 Date: May 21, 1993

§ 102(e) Date: May 21, 1993

[87] PCT Pub. No.: WO92/09281

PCT Pub. Date: Jun. 11, 1992

[30] Foreign Application Priority Data

Nov. 24, 1990 [GB] United Kingdom ............ 9025592
Nov. 24, 1990 [GB] United Kingdom ............ 9025593
Nov. 24, 1990 [GB] United Kingdom ............ 9025594
Nov. 24, 1990 [GB] United Kingdom ............ 9025595

[51] Int. Cl.$^5$ ........................................ A61K 31/4.35
[52] U.S. Cl. ........................................ 514/321
[58] Field of Search ........................................ 514/321

[56] References Cited

U.S. PATENT DOCUMENTS

4,007,196 2/1977 Christensen et al.
5,169,856 12/1992 Goto et al. ............ 514/321

FOREIGN PATENT DOCUMENTS

0188081 7/1986 European Pat. Off.
0226574 5/1988 European Pat. Off.

OTHER PUBLICATIONS

International Journal of Geriatric Psychiatry, vol. 3, 1988, John Wiley & Sons, Ltd, J. Balldin et al.: "Relationship between DST and the serotonergic system. Results from treatments with two 5-HT reuptake blockers in dementia disorders", pp. 17–26, see p. 18, col. 2, lines 15–39; p. 19, col. 2, lines 25–38.

Annals of the New York Academy of Sciences, vol. 600, Oct. 1990, (New York, US), A. J. Cross: "Serotonin in Alzheimer-type dementia and other dementing illnesses", pp. 405–417, see p. 406, table 1; pp. 412–413.

Current Therapeutic Research, vol. 25, No. 2, Feb. 1979, E. Syvalahti et al.: "Migraine headache and blood serotonin levels after administration of zimelidine, a selective inhibitor of serotonin uptake", pp. 299–310, see the whole document.

Progress in Drug Research, vol. 35, 1990, (Basel, CH), R. W. Fuller: "Drugs affecting serotonin neurons", pp. 85–108, see p. 87, paragraph 3—p. 88; p. 89, paragraph 9; p. 99, paragraph 2.

European Journal of Pharmacology, vol. 183, No. 5, Jul. 1990, M. D. Cotrim et al.: "Migraine and serotonin uptake, 3Hdelta—paroxetine and 3H—imipramine binding", p. 1917, see the whole document.

International Journal of Obesity, vol. 11, suppl. 3, Dec. 1987, C. P. L. Freeman et al.: "Fluoxetine as a treatment for bulimia nervosa", pp. 171–177, see the whole document.

*Primary Examiner*—Johann Richter
*Assistant Examiner*—John Peabody
*Attorney, Agent, or Firm*—Edward T. Lentz; Stuart R. Suter; Stephen Venetianer

[57] ABSTRACT

The method of using paroxetine or a pharmaceutically acceptable salt thereof for the treatment of senile dementia.

8 Claims, No Drawings

USE OF PAROXETINE FOR THE TREATMENT OF SENILE DEMENTIA, BULIMIA, MIGRAINE OR ANOREXIA

The present invention relates to a method for the treatment of senile dementia, bulimia, migraine or anorexia and to a compound for use in such methods.

U.S. Pat. No. 4 007 196 discloses the compound, (—)-trans-4-(4'-fluorophenyl)-3-(3'4'-methylenedioxyphenoxymethyl)piperidine, and, in Example 2, a process by which it can be prepared. The compound, which is referred to herein by its common name, paroxetine, is described in the patent as an inhibitor of 5-hydroxytryptamine uptake and, therefore, is of use in the treatment of depression. The patent also mentions that paroxetine is useful in the treatment of Parkinson's disease.

It has now been discovered that paroxetine also has potential therapeutic utility for treating senile dementia, bulimia, migraine or anorexia.

Accordingly, the present invention provides a method for treating senile dementia, bulimia, migraine or anorexia in human or non-human animals, which method comprises administering an effective, non-toxic amount of paroxetine or a pharmaceutically acceptable salt thereof, to human or non-human animals suffering from senile dementia, bulimia, migraine or anorexia.

The present invention also provides the use of paroxetine or a pharmaceutically acceptable salt thereof in the manufacture of a medicament for use in the treatment of senile dementia, bulimia, migraine or anorexia.

Examples of pharmaceutically acceptable salts of paroxetine are paroxetine hydrochloride, paroxetine hydrobromide, paroxetine acetate and paroxetine maleate. A preferred salt is crystalline paroxetine hydrochloride hemi-hydrate.

A paroxetine medicament, for use in the treatment of senile dementia, bulimia, migraine or anorexia may be prepared by admixture of paroxetine or salt thereof with an appropriate carrier, which may contain a diluent, binder, filler, disintegrant, flavouring agent, colouring agent, lubricant or preservative in conventional manner.

Preferably, the medicament is in unit dosage form and in a form adapted for use in the medical or veterinarial fields. For example, such preparations may be in a pack form accompanied by written or printed instructions for use as an agent in the treatment of senile dementia, bulimia, migraine or anorexia.

The suitable dosage range for paroxetine or a salt depends on the severity of the senile dementia, bulimia, migraine or anorexia and on the condition of the patient. It will also depend, inter alia, upon the relation of potency to absorbability and the frequency and route of administration.

Paroxetine or a salt thereof may be formulated for administration by any route, and examples are oral, rectal, topical, parenteral, intravenous or intramuscular administration. Preparations may, if desired, be designed to give slow release of paroxetine.

The medicaments may, for example, be in the form of tablets, capsules, sachets, vials, powders, granules, lozenges, reconstitutable powders, or liquid preparations, for example solutions or suspensions, or suppositories.

The medicaments, for example those suitable for oral administration, may contain conventional excipients such binding agents, for example syrup, acacia, gelatin, sorbitol, tragacanth, or polyvinylpyrrolidone; fillers, for example lactose, sugar, maize-starch, calcium phosphate, sorbitol or glycerine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid medicaments may be obtained by conventional methods of blending, filling, tabletting or the like. Repeated blending operations may be used to distribute paroxetine or a salt thereof throughout those medicaments employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, for example of gelatin containing paroxetine or a salt thereof if desired with a carrier or other excipients.

Medicaments for oral administration as liquids may be in the form of, for example, emulsions, syrups, or elixirs, or may be presented as a dry product for reconstitution with water or other suitable vehicle before use. Such liquid medicaments may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

Paroxetine or a salt thereof may also be administered by a non-oral route. In accordance with routine pharmaceutical procedure, the medicaments may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or-a solid form or concentrate which can be used to prepare an injectable formulation.

As mentioned hereinbefore, the effective dose of paroxetine depends on the severity of the senile dementia, bulimia, migraine or anorexia, the condition of the patient and on the frequency and route of administration. A unit dose wall. generally contain from 2 to 1000 mg and preferably will contain from 30 to 500 mg, in particular 20, 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of paroxetine and be administered in multiples, if desired, to give the preceding daily dose.

The present invention further provides a pharmaceutical composition for use in the treatment of senile dementia, bulimia, migraine or anorexia which comprises an effective amount of paroxetine or a pharmaceutically acceptable salt thereof and a pharmaceutically acceptable carrier. Such compositions may be prepared in the manner as hereinbefore described.

The following example demonstrates a suitable pharmaceutical composition:

EXAMPLE 1

The following were mixed together in a conventional manner and compressed into a tablet in a conventional manner.

| | |
|---|---|
| 22.88 mg | Paroxetine hydrochloride hemihydrate |
| 244.12 mg | Dibasic calcium phosphate dihydrate |
| 15.00 mg | Hydroxypropylmethyl cellulose 2910 |
| 15.00 mg | Sodium starch glycollate |
| 3.00 mg | Magnesium Stearate |
| 300.00 mg | Total tablet weight |

We claim:

1. A method for treating senile dementia in human or non-human animals, which method comprises administering an effective, non-toxic amount of paroxetine or a pharmaceutically acceptable salt thereof, to human or non-human animals suffering from senile dementia.

2. A method according to claim 1 in which the paroxetine or a pharmaceutically acceptable salt thereof is adapted fox oral administration.

3. A method according to claim 1 in which the paroxetine or a pharmaceutically acceptable salt thereof is adapted for parenteral administration.

4. A method according to claim 1 in which the paroxetine or a pharmaceutically acceptable salt thereof is in a unit dose form containing from 2 to 1000 mg of paroxetine or a pharmaceutically acceptable salt thereof.

5. A pharmaceutical composition for use in the treatment of senile demential which comprises an effective amount of paroxetine or a pharmaceutically acceptable salt thereof and a pharmaceutically acceptable carrier.

6. A pharmaceutical composition according to claim 5 which is adapted for oral administration.

7. A pharmaceutical composition according to claim 5 which is adapted for parenteral administration.

8. A pharmaceutical composition according to claim 5 wherein the paroxetine or a pharmaceutically acceptable salt thereof is in a unit dose form containing from 2 to 1000 mg of paroxetine or a pharmaceutically acceptable salt thereof.

* * * * *